United States Patent [19]

Santilli et al.

[11] 3,950,339

[45] Apr. 13, 1976

[54] SUBSTITUTED-2-(PYRIMIDINYLTHIO)ACETAMIDOXIMES AND ACETONITRILES

[75] Inventors: Arthur A. Santilli, Havertown; Anthony C. Scotese, King of Prussia, both of Pa.

[73] Assignee: American Home Products Corporation, New York, N.Y.

[22] Filed: Apr. 22, 1975

[21] Appl. No.: 570,546

Related U.S. Application Data

[63] Continuation-in-part of Ser. No. 514,676, Oct. 15, 1974, abandoned.

[52] U.S. Cl. .......................... 260/256.5 R; 424/251
[51] Int. Cl.² ..................................... C07D 239/00
[58] Field of Search ........................... 260/256.5 R

[56] References Cited
UNITED STATES PATENTS

| | | | |
|---|---|---|---|
| 3,627,891 | 12/1971 | Driscoll | 260/256.5 R X |
| 3,814,761 | 6/1974 | Santilli et al. | 260/256.5 R |
| 3,817,998 | 6/1974 | Anderson et al. | 260/256.5 R X |
| 3,859,288 | 1/1975 | DeAngelis et al. | 260/256.5 R X |

*Primary Examiner*—Leonard Schenkman
*Attorney, Agent, or Firm*—David E. Frankhouser

[57] ABSTRACT

2-(6-alkyl or phenyl-2-pyrimidinylthio)acetamidoximes, in which the 4-position is substituted with the p-chlorobenzylamino, p-methoxyphenylamino, or 1,3-benzodioxol-5-yl-methylamino group, have antiarrhythmic activity. The compounds are prepared from an appropriately substituted 2-pyrimidinylthio)acetonitrile by reaction with hydroxylamine hydrochloride.

18 Claims, No Drawings

SUBSTITUTED-2-(PYRIMIDINYLTHIO)ACETAMIDOXIMES AND ACETONITRILES

This application is a continuation-in-part of application Ser. No. 514,676, filed Oct. 15, 1974 and now abandoned.

This invention relates to chemical compounds classified in the art of chemistry as substituted-(2-pyrimidinylthio)acetamidoximes having pharmacological activity and to intermediates for the production thereof.

In its first aspect, this invention comprises chemical compounds of the molecular formula:

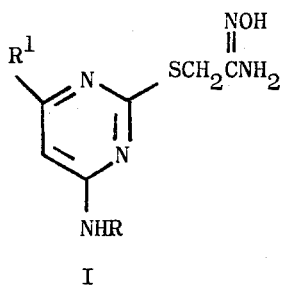

I wherein R is 4-halobenzyl, 4-methoxyphenyl, or 1,3-benzodioxol-5-ylmethyl, and $R^1$ is methyl, ethyl, propyl, or phenyl; with the provisos that when $R^1$ is propyl, R cannot be 4-methoxyphenyl, and when $R^1$ is phenyl, R cannot be 4-halobenzyl or 4-methoxyphenyl; or a pharmaceutically acceptable acid addition salt thereof.

The compounds of Formula I elevate the electrical fibrillatory threshold in anesthetized dogs demonstrating cardiac antiarrhythmic activity.

In its second aspect, this invention comprises compounds of the formula:

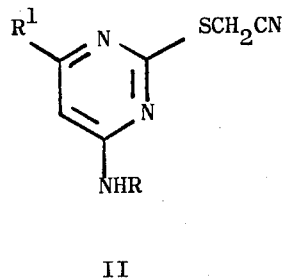

II where R is 4-halobenzyl, 4-methoxyphenyl, or 1,3-benzodioxol-5-ylmethyl and $R^1$ is methyl, ethyl, propyl, or phenyl, with the provisos that when $R^1$ is propyl, R cannot be 4-methoxyphenyl, and when $R^1$ is phenyl, R cannot by 4-halobenzyl or 4-methoxyphenyl.

In its third aspect, this invention comprises compounds of the formula:

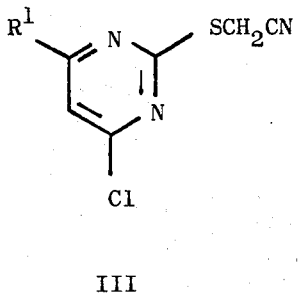

III wherein $R^1$ is methyl, ethyl, propyl, or phenyl.

The compounds of Formula II and III are intermediates for the production of the antiarrhythmic compounds of Formula I.

The compounds of Formula I are prepared from the compounds of Formula II by reaction with hydroxylamine hydrochloride in N,N-dimethylformamide in the presence of sodium carbonate. The intermediates of Formula II, where $R^1$ is methyl, ethyl, or propyl, are prepared in three steps as follows:

In step (a), a 6-alkyl-2-thiouracil, sodium salt, is condensed with 2-chloroacetamide to give a 2-(4-hydroxy-6-alkyl-2-pyrimidinylthio)acetamide. In step (b), treatment of the acetamide of step (a) with phosphorus oxychloride converts the amide group to a nitrile group and simultaneously replaces the hydroxyl group with a chloro group to afford a (4-chloro-6-alkyl-2-pyrimidinylthio)acetonitrile (III). In step (c), the reactive chlorine atom in position 4 is replaced by reaction with an appropriate amine (i.e. 4-halobenzylamine, p-anisidine, or piperonylamine). When $R^1$ is phenyl, the starting compound is 6-phenyl-2-thiouracil.

As used herein the term "alkyl" means methyl, ethyl, or propyl. "Halo" means the chlorine, bromine, iodine, or fluorine atom.

If desired the compounds of Formula I can be isolated and used for the pharmacological purposes herein described in the form of a non-toxic, pharmaceutically acceptable acid addition salts. Suitable non-toxic, pharmaceutically acceptable acids will be readily apparent to those skilled in the art.

The following examples are illustrative of the methods of preparing the compounds of the invention and of demonstrating and elliciting antiarrhythmic activity:

EXAMPLE 1

2-(4-Hydroxy-6-Methyl-2-Pyrimidinylthio)Acetamide

To a solution of 16.8 g. (0.2 mole) of sodium bicarbonate in 300 ml of water was added 22.8 g.(0.2 mole) of 6-methyl-2-thiouracil. The mixture was heated on a steam bath for 10 minutes. To this mixture was then added 18.6 g.(0.2 mole) of 2-chloroacetamide followed by 100 ml of absolute ethanol. The mixture was heated on a steam bath for 2 hours. The solution was cooled in an ice bath and the precipitate which formed was collected and recrystallized from a mixture of N,N-dimethylformamide and ethanol to afford 8 g. of product, m.p. 238°–240° d.

Analysis for: $C_7H_9N_3SO_2$: Calculated: C, 42.40; H, 4.55; N, 21.09 %. Found: C, 42.13; H, 4.23; N, 21.15.

EXAMPLE 2

2-(4-Hydroxy-6-Propyl-2-Pyrimidinylthio)Acetamide

To a solution of 8.4 g. (0.1 mole) of sodium bicarbonate in 200 ml of water was added 17.0 g. (0.1 mole) of 2-chloroacetamide and 75 ml of absolute ethanol. After heating on a steam bath for two hours, the solution was cooled and the resulting precipitate was collected and recrystallized from ethanol to afford 5.6 g. of product, m.p. 200°–203° d.

Analysis for: $C_9H_{13}N_3SO_2$: Calculated: C, 47.56; H, 5.76; N, 18.49 %. Found: C, 47.39; H, 5.82; N, 18.29.

EXAMPLE 3

(4-Chloro-6-Methyl-2-Pyrimidinylthio)Acetonitrile

To a solution of 19.4 g. (0.13 mole) of N,N-diethylaniline in 250 ml of phosphorus oxychloride was added 25.8 g (0.13 mole) of 2-(4-hydroxy-6-methyl-2-pyrimidinylthio)acetamide, the mixture was heated under reflux for 1 hour. The phosphorus oxychloride was removed in a rotary evaporator and the residue was poured onto 1 liter of cracked ice. The precipitate which resulted was collected, dried, and recrystallized from heptane to give 13.0 g. of pure white product, m.p. 62°–65°.

Analysis for: $C_7H_6N_3ClS$: Calculated: C, 42.11; H, 3.03; N, 21.04 %. Found: C, 42.12; H, 3.06; N, 21.25.

EXAMPLE 4

(4-Chloro-6-Propyl-2-Pyrimidinylthio)Acetonitrile

To a suspension of 4.5 g. (0.02 mole) of 2-(4-hydroxy-6-propyl-2-pyrimidinylthio)acetamide in 50 ml of phosphorus oxychloride was added 2.98 g. of N,N-diethylaniline. The mixture was heated for ten minutes to reflux temperature. The phosphorus oxychloride was removed in a rotary evaporator and the residue was poured into 150 ml of ice-water. The water mixture was extracted with 100 ml of ether. The ether layer was dried over magnesium sulfate, filtered and evaporated in a rotary evaporator to give an oil. A small amount of the oil was dried in vacuo without purification to afford the analytical sample.

Analysis for: $C_9H_{10}N_3ClS$: Calculated: C, 47.47; H, 4.43 N, 18.45 %. Found: C, 47.80; H, 4.51; N, 18.33.

EXAMPLE 5

[4-(p-Chlorobenzylamino)-6-methyl-2-Pyrimidinylthio]Acetonitrile

A stirred mixture of 5.97 g. (0.03 mole) of (4-chloro-6-methyl-2-pyrimidinylthio)acetonitrile, 4.2 g. (0.03 mole) of 4-chlorobenzylamine and 3.15 g. (0.03 mole) of sodium carbonate in 150 ml of absolute ethanol was heated under reflux for 6 hours. The mixture was filtered and the filtrate evaporated in a rotary evaporator. The residue was triturated with petroleum ether containing a little ethanol. The solid which crystallized was collected and recrystallized from ethyl acetate with petroleum ether added to induce precipitation affording 3.2 g. of product, m.p. 99°–101°.

Analysis for: $C_{14}H_{13}N_4SCl$: Calculated: C, 55.17; H, 4.30; N, 18.38 %. Found: C, 55.03; H, 4.38; N, 18.29.

EXAMPLE 6

[4-(p-Anisidino)-6-Methyl-2-Pyrimidinylthio]Acetonitrile

A stirred mixture of 15.0 g. (0.075 mole) of (4-chloro-6methyl-2-pyrimidinylthio)aceto nitrile, 10.0g. (0.075 mole) p-anisidine and 7.5 g. (0.075 mole) of sodium carbonate in 150 ml of ethanol was heated under reflux for five hours. The mixture was filtered and the filtrate was evaporated in a rotary evaporator. The oily residue was dissolved in ethyl acetate. Dilution of the ethyl acetate solution with petroleum ether and cooling in ice yielded a precipitate. This solid was collected and recrystallized from a mixture of benzene-petroleum ether to afford 7.2 g. of product, m.p. 128°–131°.

Analysis for: $C_{14}H_{14}N_4OS$: Calculated: C, 58.72; H, 4.93; N, 19.57 %. Found: C, 58.71; H, 5.02; N, 19.23.

EXAMPLE 7

[4-(1,3-Benzodioxol-5-Ylmethylamino)-6-Methyl-2-Pyrimidinylthio]Acetonitrile

A stirred mixture of 13.93 g. (0.07 mole) of (4-chloro-6-methyl-2-pyrimidinylthio)acetonitrile, 10.5 g. (0.07 mole) of piperonylamine and 7.42 g. (0.07 mole) of sodium carbonate in 100 ml of ethanol was heated under reflux for five hours. The mixture was filtered and the filtrate was cooled in ice. The precipitate thus formed was collected and recrystallized from absolute ethanol to give 15.7 g. of product, m.p. 115°–118°.

Analysis for: $C_{15}H_{14}N_4O_2S$: Calculated: C, 57.31; H, 4.49; N, 17.82 %. Found: C, 57.04; H, 4.40; N, 17.97.

EXAMPLE 8

[4-(p-Chlorobenzylamino)-6-Propyl-2-Pyrimidinylthio]Acetonitrile

A stirred suspension of 13.62 g. (0.06 mole) of (4-chloro-6-propyl-2-pyrimidinylthio)acetonitrile, 8.40 g. (0.06 mole) of p-chlorobenzylamine and 6.36 g. (0.06 mole) of sodium carbonate was heated under reflux in 150 ml of ethanol for five hours. The mixture was filtered and the filtrate was evaporated in a rotary evaporator. The residue was dissolved in ether (150 ml) and extracted with 150 ml of 10% concentrated hydrochloric acid solution. The ether layer was dried over magnesium sulfate, filtered and evaporated in a rotary evaporator. This residue was dissolved in benzene, diluted with a little heptane and was cooled in ice. The precipitate which formed was collected and recrystallized a second time from a benzene-heptane mixture to give 3.6 g. of product, m.p. 68°–70°.

Analysis for: $C_{16}H_{17}N_4ClS$: Calculated: C, 57.73; H, 5.15; N, 16.83 %. Found: C, 57.65; H, 5.04; N, 17.17.

EXAMPLE 9

[4-(1,3-Benzodioxol-5-Ylmethylamino)-6-Phenyl-2-pyrimidinylthio]Acetonitrile

A stirred suspension of 19.5 g (0.075 mole) of (4-chloro-6-phenyl-2-pyrimidinylthio)acetonitrile, 11.3 g (0.074 mole) of piperonylamine and 7.95 g (0.075 mole) of sodium carbonate was heated under reflux in 250 ml of ethanol for six hours. The mixture was filtered and the filtrate was cooled in ice. The precipitate was collected and recrystallized from ethanol to give 16 g of product, mp. 140°–142°.

Analysis for: $C_{20}H_{16}N_4SO_2$ Calculated: C, 63.81; H, 4.28; N, 14.88 %. Found: C, 63.49; H, 4.27; N, 14.91.

EXAMPLE 10

[4-(1.3-Benzodioxol-5-Ylmethylamino)-6-Propyl-2-Pyrimidinylthio]Acetonitrile

A stirred suspension of 13.50 g. (0.06 mole) of (4-chloro-6-propyl-2-pyrimidinylthio)acetonitrile, 9.00 g. (0.06 mole) of piperonylamine and 6.36 g. (0.06 mole) of sodium carbonate was heated under reflux for six hours. The mixture was filtered and the filtrate was evaporated in a rotary evaporator. The residue was dissolved in ethyl acetate, diluted with petroleum ether and was cooled in ice. The precipitate which formed was collected and recrystallized from a mixture of ethanol-petroleum ether to give 3.0 g. of product, m.p. 92°–94°.

Analysis for: $C_{17}H_{18}N_4O_2S$: Calculated: C, 59.63; H, 5.30; N, 16.36 %. Found: C, 59.66; H, 5.36; N, 16.34.

EXAMPLE 11

2-[4-(p-Chlorbenzylamino)-6-Methyl-2-Pyrimidinylthio]Acetamidoxime

A mixture of 10.6g. (0.035 mole) of [4-(p-chlorobenzylamino)-6-methyl-2-pyrimidinylthio]acetonitrile, 4.83 g. (0.07 mole) of hydroxylamine hydrochloride and 14.7 g. (0.14 mole) of sodium carbonate in 100 ml of N,N-dimethylformamide was heated on a steam bath for 3 hours. The mixture was filtered and the filtrate evaporated in a rotary-evaporator. The residue was triturated with petroleum ether containing a little ethyl acetate. The solid which crystallized was collected and recrystallized from ethyl acetate to give pure free base, m.p. 113°–116°. This free base was dissolved in absolute ethanol and acidified with an ethereal hydrochloric acid solution to give 3.5 g. of product, as the dihydrochloric salt, m.p. 230°–232° d.

Analysis for: $C_{14}H_{16}N_5SClO.2HCl$: Calculated: C. 40.93; H. 4.42; N, 17.05 %. Found: C, 40.60; H, 4.44; N, 16.75.

EXAMPLE 12

2-[4-(1,3-Benzodioxol-4-Ylmethylamino)-6-Methyl-2-Pyrimidinylthio]Acetamidoxime

A mixture of 6.20 g. (0.02 mole) of (4-methyl-6-piperonylamino-2-pyrimidinylthio)acetonitrile, 2.76 g. (0.04 mole) of hydroxylamine hydrochloride and 8.48 g. (0.08 mole) of sodium carbonate in 100 ml of N,N-dimethylformamide was heated on a steam bath for four hours. The mixture was filtered and the filtrate was evaporated in a rotary evaporator. The residue was triturated with ether and the insoluble material was collected and recrystallized from a mixture of ethanol-N,N-dimethylacetamide to give 3.5 g. of product, m.p. 190°–192° dec.

Analysis for: $C_{15}H_{17}N_5O_3S$:
Calculated: C, 51.86; H, 4.93; N, 20.16%.
Found: C, 51.68; H, 4.90; N, 19.98.

EXAMPLE 13

2-[4-(p-Methoxyphenylamino)-6-Methyl-2-Pyrimidinylthio]Acetamidoxime

A mixture of 11.20 g (0.04 mole) of [4-(p-anisidino)-6-methyl-2-pyrimidinylthio]acetonitrile, 5.52 g (0.08 mole) of hydroxylamine hydrochloride and 16.90 g (0.16 mole) of sodium carbonate in 150 ml of N,N-dimethylformamide was heated on a steam bath for three and one-half hours. The mixture was filtered and the filtrate was evaporated in a rotary evaporator. The residue was dissolved in ethyl acetate, diluted with petroleum ether and was cooled in ice. The precipitate which formed was collected and recrystallized from a mixture of ethanol-petroleum ether to afford 3.7 g of product, m.p. 189°–191° d.

Analysis for: $C_{14}H_{17}N_5O_2S$: Calculated: C, 52.64; H, 5.37; N, 21.93 %. Found: C, 52.74; H, 5.45; N, 22.07.

EXAMPLE 14

2-[4-(p-Chlorobenzylamino)-6-Propyl-2-Pyrimidinylthio]Acetamidoxime

A mixture of 6.60 g. (0.02 mole) of [4-(p-chlorobenzylamino)-6-propyl-2-pyrimidinylthio]acetonitrile, 2.76 g. (0.04 mole) of hydroxylamine hydrochloride and 8.48 g. (0.08 mole) of sodium carbonate in 100 ml of N,N-dimethylformamide was heated on a steam bath for three and one-half hours. The mixture was filtered, diluted with 250 ml of water and extracted with 100 ml of ether. The ether layer was dried over magnesium sulfate, filtered and evaporated in a rotary evaporator. The residue was dissolved in ethanol, diluted with petroleum ether and cooled in ice. The precipitate which formed was collected and recrystallized from a mixture of ethanol-petroleum ether to give the analytical sample, m.p. 50° dec.

Analysis for: $C_{16}H_{20}N_5ClSO$: Calculated: C, 52.52; H, 5.51; N, 19.14 %. Found: C, 52.35; H, 5.47; N, 18.94.

EXAMPLE 15

2-[4-(1,3-Benzodioxol-5-Ylmethylamino)-6-Phenyl-2-Pyrimidinylthio]Acetamidoxime

A mixture of 11.20 g. (0.03 mole) of [4-phenyl-6-(piperonylamino)-2-pyrimidinylthio]acetonitrile, 4.14 g. (0.06 mole) of hydroxylamine hydrochloride and 12.70 g. (0.12 mole) of sodium carbonate in 200 ml of N,N-dimethylformamide was heated on a steam bath for four hours. The mixture was filtered and the filtrate was evaporated in a rotary evaporator. The residue was dissolved in ethyl acetate, diluted with petroleum ether and left at room temperature overnight. The precipitate which formed was collected and recrystallized from a mixture of ethyl acetate-petroleum ether to give 4.8 g. of product, mp. 160°–163°.

Analysis for: $C_{20}H_{19}N_5O_3S$ Calculated: C, 58.66; H, 4.68; N, 17.11 %. Found: C, 58.97; H, 4.70; N, 16.77.

EXAMPLE 16

2-[4-(1,3-Benzodioxol-5-Ylmethylamino)-6-Propyl-2-Pyrimidinylthio]Acetamidoxime

A mixture of 10.20 g. (0.03 mole) of [4-(1,3-benzodoioxol-5-ylmethyl)-6-propyl-2-pyrimidinylthio]acetonitrile, 4.14 g. (0.06 mole) of hydroxylamine hydrochloride and 12.72 g. (0.12 mole) of sodium carbonate in 150 ml of N,N-dimethylformamide was heated on a steam bath for three and one-half hours. The mixture was filtered and the filtrate was evaporated in a rotary evaporator. The residue was dissolved in 100 ml. of ether and extracted with 100 ml of 10% concentrated hydrochloric acid. The ether layer was dried over magnesium sulfate, filtered and evaporated in a rotary evaporator. The residue was dissolved in ethanol, diluted with petroleum ether and cooled in ice. The precipitate which formed was collected and recrystallized from ethyl acetate to afford 2.9 g. of product, m.p. 145°–147° d.

Analysis for: $C_{17}H_{21}N_5O_3S$ Calculated: C, 54.38; H, 5.64; N, 18.65 %. Found: C, 54.17; H, 5.65; N, 18.48.

EXAMPLE 17

(4-Chloro-6-Phenyl-2-Pyrimidinylthio)Acetonitrile

To a solution of 14.9 g. (0.1 mole) of N,N-diethylaniline in 400 ml. of phosphorus oxychloride was added 26.1 g. (0.1 mole) of 2-(4-hydroxy-6-phenyl-2- pyrimidinylthio)acetamide. After being heated under reflux for one hour the phosphorus oxychloride was removed in a rotary evaporator. The residue was poured into 1000 ml. of ice-water and the precipitate was collected by filtration. The filter cake was triturated with 250 ml. of acetone with the insoluble material being removed by filtration. Dilution of filtrate with 250 ml. of water afforded a solid which was collected and recrystallized from ethyl acetate-petroleum ether to give 7 g. of material. A second recrystallization from ethyl acetate-heptane yielded the analytical sample, mp. 136°–141°.

Analysis for: $C_{12}H_8N_3SCl$ Calculated: C, 55.07; H, 3.08; N, 16.05 %. Found: C, 55.36; H, 3.30; N, 16.12.

EXAMPLE 18 the antiarrhythmic activity of the compounds of the invention is demonstrated and ellicited by the following test method:

The heart of an anesthetized dog is exposed by a left thoractomy. Bipolar electrodes are sutured to the epicardial surface of the left ventricle. The heart is stimulated with square wave pulses of 3 msec duration and frequence of 60 Hz for periods of 5 sec. Voltage is increased until fibrillation ensues. The heart is then defibrillated by DC countershock and the procedure repeated at 10 min. intervals. Drugs are administered i.v. over periods of 3 min. and fibrillatory threshold examined 10 min. after start of injection of each dose. Effective antiarrhythmic agents elevate the fibrillatory threshold.

When tested as set forth above the compounds described in the preceding examples elevate the electrical fibrillatory threshold at a dose of 10–20 mg/kg. body weight.

What is claimed is:

1. A compound of the formula

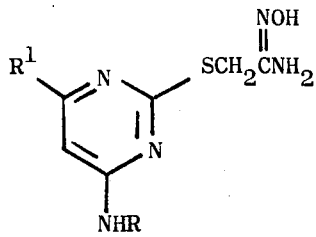

wherein R is 4-halobenzyl, 4-methoxyphenyl, or 1,3-benzodioxol-5-ylmethyl, and $R^1$ is methyl, ethyl, propyl, or phenyl; with the provisos that when $R^1$ is propyl, R cannot be 4-methoxyphenyl, and when $R^1$ is phenyl, R cannot be 4-halobenzyl or 4-methoxyphenyl; or a pharmaceutically acceptable acid addition salt thereof.

2. A compound as defined in claim 1 which is 2-[4-(p-chlorobenzylamino)-6-methyl-2-pyrimidinylthio]acetamidoxime.

3. A compound as defined in claim 1 which is 2-[4-(1,3-benzodioxol-4-ylmethylamino)-6-methyl-2-pyrimidinylthio]acetamidoxime.

4. A compound as defined in claim 1 which is 2-[4-(p-methoxyphenylamino)-6-methyl-2-pyrimidinylthio]acetamidoxime.

5. A compound as defined in claim 1 which is 2-[4-(p-chlorobenzylamino)-6-propyl-2-pyrimidinylthio]acetamidoxime.

6. A compound as defined in claim 1 which is 2-[4-(1,3-benzodioxol-5-ylmethylamino)-6-phenyl-2-pyrimidinylthio]Acetamidoxime.

7. A compound as defined in claim 1 which is 2-[4-(1,3-benzodioxol-5-ylmethylamino)-6-propyl-2-pyrimidinylthio]acetamidoxime.

8. A compound of the formula:

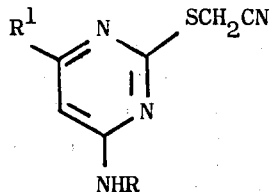

wherein R is halobenzyl, 4-methoxyphenyl, or 1,3-benzodioxol-5-ylmethyl, and $R^1$ is methyl, ethyl, or propyl.

9. a compound as defined in claim 8 which is [4-(p-chlorobenzylamino)-6-methyl-2-pyrimidinylthio]acetonitrile.

10. A compound as defined in claim 8 which is [4-(p-anisidino)-6-methyl-2-pyrimidinylthio]acetonitrile.

11. A compound as defined in claim 8 which is [4-(1,3-benzodioxol-5-ylmethylamino)-6-methyl-2-pyrimidinylthio]acetonitrile.

12. A compound as defined in claim 8 which is [4-(p-chlorobenzylamino)-6-propyl-2-pyrimidinylthio]acetonitrile.

13. A compound as defined in claim 8 which is [4-(1,3-benzodioxol-5-ylmethylamino)-6-phenyl-2-pyrimidinylthio]acetonitrile.

14. A compound as defined in claim 8 which is [4-(1,3-benzodioxol-5-ylmethylamino)-6-propyl-2-pyrimidinylthio]acetonitrile.

15. A compound of the formula:

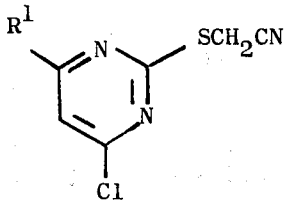

wherein R is methyl, ethyl, propyl, or phenyl.

16. A compound as defined in claim 15 which is (4-chloro-6-methyl-2-pyrimidinylthio)acetonitrile.

17. A compound as defined in claim 15 which is (4-chloro-6-propyl-2-pyrimidinylthio)acetonitrile.

18. A compound as defined in claim 15 which is (4-chloro-6-phenyl-2-pyrimidinylthio)acetonitrile.

* * * * *